United States Patent [19]
Clarke et al.

[11] Patent Number: 6,002,067
[45] Date of Patent: Dec. 14, 1999

[54] TRANSGENIC MOUSE MODEL FOR IDURONIDASE DEFICIENCY AND METHODS OF MAKING AND USING SAME

[75] Inventors: Lorne A. Clarke, Richmond; Frank Jirik, Vancouver, both of Canada

[73] Assignee: The University of British Columbia, Vancouver, Canada

[21] Appl. No.: 08/858,942

[22] Filed: May 20, 1997

Related U.S. Application Data

[60] Provisional application No. 60/017,156, May 20, 1996.

[51] Int. Cl.⁶ .................................................... A61K 67/00
[52] U.S. Cl. .................................. 800/18; 800/3; 800/9; 800/25
[58] Field of Search .................................. 800/2, DIG. 3, 800/18, 3, 9, 25; 435/172.3

[56] References Cited

PUBLICATIONS

Capecchi, MR. Targeted gene replacement. Scientific American, vol. 270, pp. 34–41, Mar. 1994.

Clarke, LA, et al. Genomic organization of the murine alpha–L–iduronidase gene: Identification of an overlapping transcript. Journal of Investigative Medicine, vol. 43 (Suppl. 1), p. 163A, 1995.

Westphal, H. Transgenic mammals and biotechnology. FASEB J. vol. 3, pp. 117–120, 1989.

Eck, SL, and Wilson, JM. Gene–based therapy. Goodman and Gilman's The Pharmacological basis of therapeutics, 9th ed. McGraw–Hill, New York, NY, pp. 77–101, 1995.

Pagano, RE and Weinstein, JN. Interactions of liposomes with mammalian cells. Annual Rev Blophys Bioeng, vol. 7, pp. 435–468, 1978.

Moens, CB, et al. Defects in heart and lung development in compound heterozygotes for two different targeted mutations at the N–myc locus. Development, vol. 119, pp. 485–493, 1993.

Clarke et al., "Mutation Analysis of 19 North American Mucopolysaccharidosis Type I Patients: Identification on Two Additional Frequent Mutations", Human Mutation 3: 275–282 (1994).

Clarke et al., "Murine α–L–Iduronidase: cDNA Isolation and Expression" Genomics 24: 311–316 (1994).

Clark et al. "Murine Mucopolysaccharidosis Type I: targeted disruption of the murine α–L–Iduronidase gene", Human Molec Genetics 6: 503–511 (1997).

*Primary Examiner*—Deborah Crouch
*Assistant Examiner*—Michael C. Wilson
*Attorney, Agent, or Firm*—Oppedahl & Larson LLP

[57] ABSTRACT

A mouse which is homozygous for a disruption in the IDUA gene, but which has normal expression for the SAT-1 gene can be used for evaluating therapeutic agents for use in treating mucopolysaccharidosis Type I, by administering the therapeutic agent to the mouse, and evaluating the mouse for tissue pathology associated with iduronidase deficiency. The mouse can also be used for evaluating the ability of a targeting system to deliver a therapeutic agent to selected tissues or organs by administering an effective iduronidase replacement therapy coupled to the targeting system to a mouse which is homozygous for a disruption in the IDUA gene, but which has normal expression for the SAT-1 gene; and evaluating at least the selected tissue or organ from the mouse for pathology associated with iduronidase deficiency. Targeting systems which can be evaluated using this methodology include targeting moieties which selectively bind to or associate with selected cell types and in vivo and ex vivo gene therapy systems.

17 Claims, 1 Drawing Sheet

TRANSGENIC MOUSE MODEL FOR IDURONIDASE DEFICIENCY AND METHODS OF MAKING AND USING SAME

This application is a section 111(a) application claiming priority from U.S. Provisional Patent Application No. 60/017,156 filed May 20, 1996.

BACKGROUND OF THE INVENTION

This application relates to genetically engineered mice which are useful as models for generalized lysosomal storage disorders, and in particular for iduronidase deficiency, and to methods of making and using such genetically engineered mice in the evaluation of the therapies for the treatment of such disorders and for evaluation of systems for tissue specific delivery of the therapeutic agents.

Deficiency of α-L-iduronidase (IDUA) underlies a group of autosomal recessive lysosomal storage disorders termed mucopolysaccaridosis type I (MPS I). MPS I is considered to be the prototypical MPS disorder and represents the most common MPS subtype, occurring at a frequency of approximately 1/100,000 in most populations. The spectrum of clinical features in MPS I, ranges from severe mental retardation with hepatosplenomegaly, dysostosis multiplex, corneal clouding, cardiac involvement and death in early childhood to milder symptoms consisting of corneal clouding, hearing loss, and mild visceral involvement with normal intelligence and life span. Hurler syndrome (MPS I H) represents the most common and severe manifestation of this enzyme deficiency with Scheie syndrome (MPS I S) representing the more mild form of the disease. Many patients follow an intermediate phenotype between that of Hurler and Scheie syndromes.

MPS I has been described in both a feline and canine model. Haskins et al., *Ped. Res.* 13: 1294–1297 (1979); Spellacy et al., *Proc. Nat'l. Acad. Sci.* (*USA*) 80:6091–6095 (1983). The canine model has been well characterized and has been useful in the study of the role of bone marrow transplantation in MPS I as well as early studies of direct enzyme replacement. These animal studies, as well as the observations of the effect of bone marrow transplantation in humans, indicates that the development of enzyme replacement regimes are likely to lead to advancements in the therapy of MPS disorders. Kakkis et al., *Biochem. Mol. Med.* 58: 156–167 (1996); Shull et al., *Proc. Nat'l Acad. Sci.* (*USA*) 91: 12937–12941 (1994). The high cost of canine and feline animal models combined with their relatively long life span, however, makes them less than ideal for this purpose. Thus, it would be advantageous to have a small animal model for evaluating therapeutics for MPS I. It is an object of the present invention to provide a mouse model for this purpose.

SUMMARY OF THE INVENTION

We have developed a mouse which is homozygous for a disruption in the IDUA gene, but which has normal expression for the SAT-1 gene. The mouse can be used for evaluating therapeutic agents for use in treating mucopolysaccharidosis Type I, by administering the therapeutic agent to the mouse, and evaluating the mouse for tissue pathology associated with iduronidase deficiency. The mouse can also be used for evaluating the ability of a targeting system to deliver a therapeutic agent to selected tissues or organs by administering an effective iduronidase replacement therapy coupled to the targeting system to a mouse which is homozygous for a disruption in the IDUA gene, but which has normal expression for the SAT-1 gene; and evaluating at least the selected tissue or organ from the mouse for pathology associated with iduronidase deficiency. Targeting systems which can be evaluated using this methodology include targeting moieties which selectively bind to or associate with selected cell types and in vivo and ex vivo gene therapy systems.

DETAILED DESCRIPTION OF THE INVENTION

Figure 1:
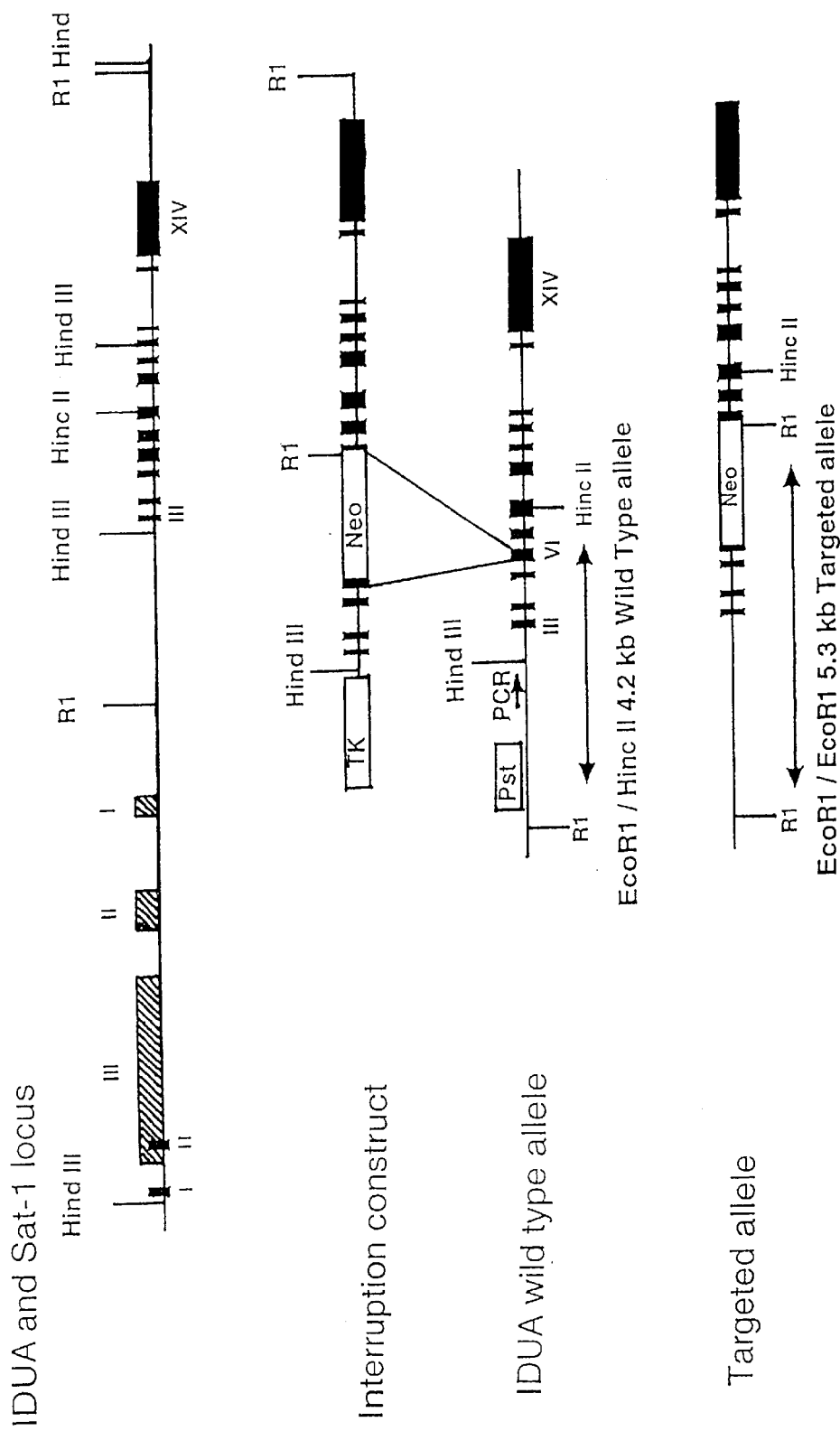
FIG. 1 shows a targeting vector useful in preparing Iduronidase deficient strains of mice.

The cDNA encoding murine IDUA has been previously identified and characterized. Clarke et al., "Murine α-L-Iduronidase: cDNA Isolation and Expression", *Genomics* 94: 311–316 (1994). This information served as the starting point for the development of the mouse model of the present invention. However, the development of the mouse model was complicated by the fact that the IDUA gene overlaps with a gene for a hepatic sulfate transporter (SAT-1). To avoid complicating effects that might arise as a result of disruption in both the SAT-1 and IDUA genes, great care had to be taken to develop a strain in which only the IDUA gene was disrupted. We have now developed such a strain of mice which are homozygous for a disruption in the IDUA gene and which have apparently normal levels of expression of the SAT-1 gene.

IDUA deficient mice were generated by gene targeting in R1 murine embryo stem cells (ES) (Nagy, et al., *Proc. Nat'l Acad, Sci* (*USA*) 90: 8424–8428 (1993)). The genomic region surrounding IDUA was fully characterized prior to the construction of a targeting vector. The genes for murine IDUA and SAT-1 are contained within a 15 KB genomic region and are read from opposite strands of DNA. The IDUA gene spans the entire region and consists of 14 exons that are separated into two clusters, one cluster containing exons I–II the other containing exons III–XIV. Intron II of IDUA separates these two clusters and is 10.5 kb in length. The SAT-1 gene consists of three exons spanning 6 kb. SAT-1 exons I and II are contained within IDUA intron II with exon III of SAT-1 beginning within IDUA intron II and extending into intron I of IDUA. Thus the entire IDUA exon II is contained within exon III of SAT-1. The overlap segment of the two genes consists of a coding exon of IDUA and a portion of the 3' UTR of sat-1.

Although the regulatory sequences of the SAT-1 gene are not known, the 5'-end of SAT-1 is a least 4 kb from the beginning of exon III of IDUA. We therefore elected to disrupt the IDUA gene in exon VI, such that the SAT-1 gene is at least 5 kb from the site of the targeted disruption.

To further minimize possible effects on SAT-1 expression, exon VI was targeted using an interruption type construct rather a deletion construct. Thus, a targeting vector containing both Pgk-Neo and Pgk-TK was made with IDUA exon VI interrupted by the neomycin resistance cassette (FIG. 1). Other neo cassettes with different promoters could also be used, as well as any marker developed for use in embryo stem cells. After double selection, ES clones that had undergone homologous recombination were identified by PCR analysis and confirmed by Southern blot. Homozygote IDUA –/– mice were generated by breeding heterozygote offspring of the chimaeras.

Enzyme assays for iduronidase were performed on both liver and tail clippings using the fluorogenic substrate 4-methylumbelliferyl-α-iduronide. The disruption of IDUA exon VI has led to no detectable enzyme activity in either the liver or the tail clippings from −/− mice. Liver from one +/− mouse revealed 50% enzyme activity as compared to normal controls. Although the use of this enzyme determinant does not distinguish between Hurler and Scheie syndrome in humans, the fact that these mice show early generalized pathology indicates that the murine phenotype is representative of the severe human phenotype.

The level of IDUA mRNA expression in normal human or murine tissues is not easily detectable by Northern analysis (Clarke et al., *Genomics* 24: 311–316 (1994); Scott, H. F., PNAS 88: 9695–9699 (1991)). We have analyzed by RT-PCR the expression of IDUA in +/+, +/− and −/− 4 weeks old mice. The −/− mice show no expression of IDUA message, while expression is seen in both the +/− mice and the +/+ mice. There is no evidence for alternative splicing of exon VI in humans and sequence analysis of murine IDUA reveals that direct splicing of exon V to VII would result in disruption of the reading frame.

SAT-1 is reported (Bissig et al., *J. Biol. Chem.* 269: 3017–3021 (1994)) to be expressed primarily in liver and kidney of the rat. To address the concern about the possible effects of IDUA disruption on the expression of SAT-1, we performed Northern analysis and RT-PCR analysis of RNA from liver and kidney from IDUA −/−, −/+ and +/+ mice. No evidence of altered expression of SAT-1 from the targeted allele was observed. Therefore it is unlikely that altered expression of SAT-1 exists in this model.

The homozygous mutant IDUA −/− mice have many phenotypic indicators which can be used as indicators of the success of a therapy in overcoming the IDUA deficiency. These indicators include the gross physiognomy of the mice, the appearance of lysosomes within many tissues of the mice, and the elevated excretion of glycosaminoglycan (GAG).

Homozygous mutant mice appear smaller than their litter mates as early as 4 weeks of age. At this age, there appears to be an early effect on the shape of the face with evidence of shortness to the snout and thickness to the digits. These facial features have also been noted as early findings in the β-glucuronidase deficient (MPS VII, Sly disease) mouse. In the MPS VII mouse model, severe features i.e severe growth retardation, joint disease and obvious facial dysmorphism are not seen until approximately 8–12 weeks of age. Therefore the features seen in our mice are in keeping with the observations in the MPS VII mouse. Radiographs of an IDUA −/− and −/+ mouse at 4 weeks of age reveal evidence of dysostosis of the ribs with anterior flaring and widening of the shafts reminiscent of the oar shaped ribs seen as an early finding in Hurler syndrome. The vertebrae appeared normal, and there does not appear to be obvious limb shortening as noted in the MPS VII mouse. Early skeletal changes in patients with iduronidase deficiency can be subtle with more progressive bone pathology in early infancy. Therefore further studies of the skeleton in the IDUA −/− mice as they age, are needed to determine whether the skeletal pathology in this model, will mimic that of the human deficiency.

We have performed pathologic examination of various organs in 4 and 8 week old +/− and −/− mice. All tissues analyzed showed evidence of abnormal lysosomal storage. (Table 1). There was no evidence of gross hepatosplenomegaly at either time point, although by 8 weeks of age the liver of IDUA −/− animals appeared duller in color and lacked the pinkish sheen of normal liver.

TABLE 1

| Organ | Cell Type | 4 weeks | 8 Weeks |
|---|---|---|---|
| Liver | Kupffer Cell | +++ | +++ |
| | Hepatocyte | 0 | ++ |
| Spleen | Sinusoidal Lining Cells | +++ | +++ |
| | Endothelial Cells | ± | + |
| Kidney | Glomerular epithelium | ± | + |
| | Interstitial Fibroblasts | ++ | +++ |
| Cartilage | | ++ | +++ |
| Bone | Chondrocytes | +++ | +++ |
| | Osteoblasts | ++ | ++ |
| Brain | Glial cells | ++ | +++ |
| | Neurons | 0 | ++ |

At 4 weeks of age, the most significant pathology occurs in the reticuloendothelial system noted by lysosomal storage in Kupffer cells, splenic sinusoidal lining cells, lung macrophages and glial cells. In the liver, lysosome-laden Kupffer cells were readily found at 4 weeks of age with very little evidence of significant hepatocyte storage. By 8 weeks of age, further progression of storage within the reticuloendothelial system had occurred and there was now evidence of significant hepatocyte vacuolation. At this age 15 to 20% of the cytoplasm of the hepatocytes appeared to be taken up by lysosomes, as contrasted to very few discernible lysosomes within normal liver samples. Spleen cells from 8 week old IDUA −/− mice also showed markedly swollen lysosomes within most cells of the sinusoids.

At 4 weeks of age abnormal lysosomal storage cab be found in the glial cells of the cortex with no appreciable lysosomal accumulation within the neurons. At 8 weeks of age, however, cytoplasmic vacuolation could be seen within the Purkinje cells of the cerebellum, neurons of the cerebral cortex, glial cells as well as cells of the leptomeninges. Within the cerebellum of IDUA −/− mice, every Purkinje cell detected contained cytoplasmic vacuoles by 8 weeks of age, although there was no major effect on the total cytoplasmic volume nor evidence of disturbed cellular architecture. Lysosomes were not detectable in normal animals at this age.

Massive lysosomal storage was also seen within chondrocytes found within both the articular surfaces of bones as well as the trachea as early as 4 weeks.

Evaluation of GAG in the urine of IDUA +/+ mice and IDUA −/− mice revealed that the amount of GAG relative to creatinine in the urine was substantially increased in IDUA −/− mice. (Table 2). Thus, measurement of GAG can serve as a non-invasive means for monitoring mice during the course of a therapeutic regimen prior to sacrificing of the mouse for tissue and organ analysis.

TABLE 2

| Genotype | mean ug GAG/mg creatinine (range) |
|---|---|
| −/− (n = 5) | 740 (538–932) |
| +/+ (n = 5) | 255 (169–324) |

Because of the wide variety of phenotypic and pathologic manifestations of the IDUA −/− genotype, the murine models which are the subject of this application provide an important and versatile model system for the testing and development of enzyme replacement regimes for mucopolysaccharide and other lysosomal storage diseases. Thus, the mice of the invention can be used for evaluating a therapeutic agent for use in treating mucopolysaccharidosis Type I. This evaluation is accomplished by administering the therapeutic agent to a mouse which is homozygous for a disruption in the IDUA gene, but which has normal expression for the SAT-1 gene, and evaluating the mouse for tissue pathology or other indicators associated with iduronidase deficiency.

Such administration can be performed by any route, including intravenous, intramuscular, oral, or intraperitoneal administration. As used herein, the term "administering" also encompasses the use of autologous and heterologous implants of tissue or pseudo-organs. Autologous implants of genetically modified fibroblasts, i.e., neo-organs, have been shown to produce stable expression of lysosomal enzymes effective for amelioration of symptoms in the beta-glucuronidase-deficient MPS VII mouse model. Moullier et al., Nature Genet. 4: 154–159 (1993). Further, the term "administering" encompasses the use of any other agent, be it viral, infectious or chemical that would promote the transfer of either a protein or a nucleic acid in to a cell.

Non-limiting examples of the types of MPS I therapeutic agents which could be evaluated using the mice and method of the invention include direct enzyme replacement with IDUA or IDUA analogs, IDUA or IDUA analogs coupled to targeting systems for directing the IDUA (or analog) to specific tissues or organs, and in vivo or ex vivo gene therapy techniques, including the use of neo-organs producing IDUA or an IDUA-analog, myoblast expression of IDUA or an IDUA analog, bone marrow transplantation and vector-mediated gene transfer.

In addition to the testing of MPS I therapies, the wide spread tissue pathology which occurs in the mice of the present invention in the absence of iduronidase makes these mice useful for testing targeted delivery systems which might be employed in the treatment of other disease and conditions. For example, if one wished to test a targeting system for delivery of therapeutic agents to the brain, that targeting system would be combined with iduronidase and administered to an IDUA disrupted mouse in accordance with the invention. After a period of time, the mouse is sacrificed and the tissues of the brain evaluated for pathology associated with iduronidase deficiency and for iduronidase activity. For example, brain tissue can be examined for abnormal lysosomal storage by microscopic examination, or assayed biochemically for iduronidase activity. Absence of such pathology (or reduction relative to a control), would indicate that the targeting system is effective to deliver therapeutic agents to the brain, particularly in view of the observation (Example 4 below) that direct administration of IDUA to IDUA -/- mice does not result in an increase in enzyme activity in the brain. Evaluation of other tissues for pathology associated with iduronidase deficiency would provide an indication of the selectivity of the targeting system.

Although evaluation of targeting systems for the brain is a very significant application of the method of the invention because of the many disorders involving the brain and because of the existence of the blood brain barrier and the many types of cells making up the central nervous system, the method of the invention can also be applied to cells of other types. Thus, for example, targeting systems intended to deliver therapeutic agents to kidney cells, liver cells, or other organs and tissues of the body can also be evaluated using the model system and method of the invention.

The method of evaluating targeting systems can be applied to any type of targeting system, including targeting systems which have a target-specific affinity label such as a hormone or antibody coupled to a therapeutic agent and systems for introducing expressible DNA into cells. Thus, the invention is useful for testing viral expression vectors such as retroviral vectors, adenovirus, adeno-associated virus and herpes virus vectors, as well as herpes applicons that are tailored to carry the iduronidase gene or cDNA. The invention is also useful for testing liposomal targeting systems by complexing purified iduronidase enzyme can be complexed with cationic lipids or other liposome components and administering the product to the model. Other targeting systems which could be evaluated include system for delivery of raw DNA used for genetic immunization and infectious vectors.

In each of these targeting systems, the model mice of the invention make it possible to evaluate the tissue specific distribution pattern of the targeting system and also the duration of efficacy. For example, the model mice of the invention provide a mechanism for studying the stability of a therapeutic genetic integration.

EXAMPLE 1

PREPARATION OF THE MOUSE Construction of the Targeting Vector

A targeting vector of the replacement type was constructed from genomic fragments of the murine gene that had been cloned into the vector BlueScript (TM). The targeting vector is pictured in FIG. 1. The PGK-Neo cassette was introduced into a Bst EII site within exon VI of IDUA by blunt cloning. The TK cassette was introduced in to the BlueScript backbone. Gene targeting and generation of homozygous mice: R1 embryo stem cells (a gift from A. Nagy. Mt. Sinai Hospital Research Inst. Toronto, Canada) at passage 9 were grown on irradiated fibroblasts. 1×10$^7$ cells were electroporated in a 1 ml cuvette at 0.4 kV and 25 uF. Cells were then plated onto gelatin coated dishes and selected for resistance to neomycin and ganciclovir. Resistant clones were further characterized by Southern blot of prepared DNA with the Pst I fragment depicted in FIG. 1 as a probe. Targeted clones were expanded and used to inject 9–10 cells into 3.5 day p.c. blastocysts from C57B16 mice. The resulting chimeric males were then mated with C57B16 females. The resulting offspring were analyzed by Southern analysis of tail DNA to identify heterozygotes. Male and female heterozygotes were then mated to produce homozygous mice.

EXAMPLE 2

Liver and tail clippings of the homozygous mice were analyzed for iduronidase activity using 4 methylumbelliferyl α-L-iduronide (4-MUI) as a substrate in accordance with the protocol described in Hopwood, J. J., Clin. Sci. 62: 193–201 (1982). See also "Enzymes that degrade heparin and heparin sulfate," in "Heparin: Chemical and Biological Properties, Clinical Applications" (Lane and Lindahl eds.) pp. 190–229, Arnold, London (1989).

Tissue is homogenized in distilled water and the supernatant sonicated. This lysate is then assayed for IDUA activity with the 4 MUI substrate. Cleavage of the 4-MUI substrate by iduronidase results in the formation of 4-methylumbelliferone which is detected by its fluorescence.

EXAMPLE 3

IDENTIFICATION OF IDUA/SAT-1 GENE STRUCTURE

To evaluate the murine IDUA genomic sequence, a 129J/Sv genomic library constructed in Lambda Dash II- (Stratagene) was screened using 2 separate probes from the murine IDUA cDNA (Clarke et al., 1994). Two phage isolates were identified each containing 15 kb genomic inserts. The clones were analyzed by restriction mapping with probes constructed from various fragments of the murine cDNA.

The two clones represented overlapping genomic fragments that spanned 25 kb of DNA and contained the entire IDUA gene. Various fragments were purified and cloned into Bluescript vector for further analysis. The nucleotide sequence of 14 kb of IDUA including all exons and introns except for a small portion of intron II was determined. IDUA spans 15 kb of DNA and comprises 14 exons, the intron exon boundary sequences follow the consensus splice site sequences (Senapathy et al., *Methods in Enzymology* 183: 252–278 (1990)). The genomic architecture of the murine IDUA gene is virtually identical to that of the human and canine. The exons are organized into two segments, one segment 1 kb in length, containing exons I and II, the other 4.5 kb in length consisting of exons III–IV. The two segments are separated by a 10.5 kb intron. The exons range in size from 77 bp to 1285 bp with some of the smallest reported introns 72 bp to 10 kb. There are two base changes within the previously published murine cDNA coding sequence and the 129J/Sv sequence reported here, one changes an amino acid; GCA to GCG (at A539 - T) the other is a silent change GAG to GAA (E25). It is unlikely that the previously reported murine cDNA (Clarke, et al., 1994) represents a full length transcript as the genomic sequence reported here reveals a more distal ATG which provides the additional amino acids proposed for the leader sequence. With the use of the more distal ATG the murine leader sequence is comparable to that reported for the human and canine genes and is not truncated as originally reported.

Three repeat sequences were identified within IDUA; an imperfect repeat within intron 10, $(AGGG)_8(TGGG)_1(AGG)_1(AGGG)_8$ which was not polymorphic; a (CA)n repeat within the 3' UTR which was found to be polymorphic; and a 47 bp repeat within intron 12 that is also polymorphic.

The 5' flanking sequence of IDUA is similar to that reported for other housekeeping genes. There is no TATA or CAAT box present but there is evidence of 1 GC box. There is a 12 bp region (CGGAGGCGGAAC) 55 bp from the start site that is also represented in both the canine and human 5' flanking regions.

The genomic sequence of the murine Sat-1 gene was revealed upon sequencing 9 kb of the 10 kb intron II of IDUA. Sequence analysis, with comparison to the published rat sat-1 cDNA sequence, revealed that SAT-1 spans 6 kb of DNA and consists of 3 exons. The intron exon boundaries were consistent with established consensus splice sites sequences (Senapathy et al., 1990). The entire exon I represents 5' UTR with part of exons II and III consisting of translated sequence.

The predicted protein is 704 amino acids in length and shows 34 differences from the published rat protein sequence (Bissig et al, 1994). The 3' UTR of the murine gene is very similar in sequence to that of the rat.

Using a fragment of Sat-1 exon II as a probe, a murine liver, oligo dT primed library (Stratagene C57B6/CBA) cDNA library was screened. Five cDNA's were isolated and sequenced. Comparison of the CDNA sequence to that of the genomic revealed that three of the five cDNAs were initiated from the "A" rich region, (AAACAAAAAACAAAA-CAAAACA), in SAT-1 exon III and thus were likely artifacts from the oligo dT priming of the library. Two cDNAs originated from the true polyadenylation site within intron II of IDUA and contained the IDUA exon II in antisense orientation. There were no amino acid differences noted between the 129J/Sv derived SAT-1 protein sequence and that of the C57B6/CBA cDNA derived sequence.

EXAMPLE 4

IDUA –/– mice were injected with a single injection of 14,000 units of purified human iduronidase via the tail vein. The animals were killed 6 hours later and entire organs were used to produce tissue lysates which were analyzed to determine IDUA activity. Table 3 shows the distribution of enzyme activity in the injected –/– mice and in a IDUA +/– control as the raw measured activity, and as a percentage of total enzyme activity. Table 4 shows the specific activity in each tissue.

The data in Tables 3 and 4 show that enzyme distribution can be increased in all tissues except the brain by injection of enzyme in a reproducible distribution pattern. This can serve as a baseline for the evaluation of targeting and expression systems.

TABLE 3

| TISSUE | Total Induronidase Activity in Injected IDUA –/– Mouse (nmole/hr) | % of Total Injected | Total Iduronidase Activity in Injected IDUA +/– Mouse (nmole/hr) | % of Total Activity |
|---|---|---|---|---|
| liver | 13552.5 | 94.50 | 49.33 | 26.61 |
| spleen | 296.76 | 2.07 | 20.87 | 11.26 |
| kidney | 204.32 | 1.42 | 12.14 | 6.55 |
| small bowel | 93.99 | 0.66 | 22.34 | 12.05 |
| heart | 38.06 | 0.27 | 3.15 | 1.70 |
| large bowel | 36.27 | 0.25 | 8.98 | 4.84 |
| lung | 28.12 | 0.20 | 8.2 | 4.42 |
| stomach | 9.06 | 0.06 | 7.38 | 3.98 |
| tail | 3.94 | 0.03 | 0 | 0.00 |
| muscle | 0.62 | 0.00 | 4.48 | 2.42 |
| brain | 0.61 | 0.00 | 6.54 | 3.53 |
| ear | 0.35 | 0.00 | 0.71 | 0.38 |
| whole body | 77.29 | 0.54 | 42.68 | 23.02 |
| TOTAL | 14341.9 | 100.00 | 185.38 | 99.99 |

TABLE 4

| Tissue | Activity nmol/hr/mg prot | |
| --- | --- | --- |
| | injected +/− | non injected +/− |
| Small bowel | 6.68 | 1.07 |
| Tail | 8.46 | 37.75 |
| Heart | 4.02 | 0.36 |
| Kidney | 8.96 | 0.49 |
| Liver | 14.73 | 0.23 |
| Lung | 2.33 | 0.72 |
| Large bowel | 1.78 | 1.28 |
| Whole body | 0.83 | 0.59 |
| Brain | 0.05 | 0.57 |
| Spleen | 25.16 | 2.00 |
| Ear | 0.47 | 1.03 |
| Muscle | 0.10 | 0.43 |

We claim:

1. A transgenic mouse which has normal expression of the SAT-1 gene and whose genome is homozygous for a disruption of the IDUA gene, wherein said disruption causes said mouse to develop a symptom of iduronidase deficiency.

2. The mouse of claim 1, wherein the IDUA gene is disrupted in exon VI.

3. The mouse of claim 2, wherein the IDUA gene is disrupted by the insertion of a marker cassette within exon VI.

4. The mouse according to claim 3, wherein the marker cassette is a neomycin resistance marker cassette.

5. A method of evaluating a therapeutic agent for treating iduronidase deficiency comprising
   a) administering an agent to a transgenic mouse which has normal expression of the SAT-1 gene and whose genome is homozygous for a disruption of the IDUA gene, wherein said disruption causes said mouse to develop a symptom of iduronidase deficiency and
   b) evaluating the effect of said agent on a symptom of iduronidase deficiency exhibited by said mouse.

6. The method according to claim 5, wherein the IDUA gene is disrupted in exon VI.

7. The method according to claim 6, wherein the IDUA gene is disrupted by the insertion of a marker cassette within exon VI.

8. The method according to claim 7, wherein the marker cassette is a neomycin resistance marker cassette.

9. A method for evaluating a targeting system for delivering a therapeutic agent for treating iduronidase deficiency to a selected tissue or organ comprising
   a) administering an agent coupled with a targeting system to a transgenic mouse which has normal expression of the SAT-1 gene and whose genome is homozygous for a disruption of the IDUA gene, wherein said disruption causes said mouse to develop a symptom of iduronidase deficiency and
   b) evaluating a tissue or organ from said mouse for a symptom associated with iduronidase deficiency.

10. The method according to claim 9, wherein the selected tissue or organ is brain.

11. The method according to claim 9, wherein the IDUA gene is disrupted in exon VI.

12. The method according to claim 11, wherein the IDUA gene is disrupted by the insertion of a marker cassette within exon VI.

13. The method according to claim 12, wherein the marker cassette is a neomycin resistance marker cassette.

14. The method according to claim 9, wherein the targeting system comprises a target-specific affinity label coupled to iduronidase.

15. The method of claim 9 wherein the agent is a viral expression vector encoding iduronidase.

16. The method according to claim 9, wherein the targeting system comprises a liposome coupled to iduronidase.

17. A method for making a transgenic mouse which has normal expression of the SAT-1 gene and whose genome is homozygous for a disruption of the IDUA gene comprising the steps of:
   a) preparing a targeting vector in which exon VI of the IDUA gene is disrupted by insertion of a selectable marker,
   b) introducing said targeting vector into mouse embryonic stem cells and selecting clones using the selectable marker, and
   c) cross-breeding chimeras to produce an offspring mouse which has normal expression of the SAT-1 gene and whose genome is homozygous for a disruption in the IDUA gene wherein said disruption causes said mouse to develop a symptom of iduronidase deficiency.

* * * * *